United States Patent [19]
Felder et al.

[11] Patent Number: 5,792,088
[45] Date of Patent: Aug. 11, 1998

[54] MEDICAL DRESSING SYSTEM

[76] Inventors: Merrylee G. Felder, 27 Linden Rd., Seekonk, Mass. 02771; Caroline Glicksman, 610 Holly Hill Dr., Brielle, N.J. 08730

[21] Appl. No.: 504,065

[22] Filed: Jul. 18, 1995

[51] Int. Cl.$^6$ .................................................. A61F 5/00
[52] U.S. Cl. ........................ 602/41; 602/61; 206/441; 128/849
[58] Field of Search .......................... 602/41–66, 74, 602/75, 79; 128/846, 849, 855, 869, 874, 877, 878, 888, 889

[56] References Cited

U.S. PATENT DOCUMENTS

| | | |
|---|---|---|
| 3,693,618 | 9/1972 | Madden . |
| 3,968,803 | 7/1976 | Hyman . |
| 4,281,650 | 8/1981 | Spiegelberg . |
| 4,627,426 | 12/1986 | Wegener et al. . |
| 4,630,610 | 12/1986 | Fletcher . |
| 5,242,433 | 9/1993 | Smith et al. . |
| 5,275,284 | 1/1994 | Onotsky . |

*Primary Examiner*—Richard J. Apley
*Assistant Examiner*—Kim M. Lee
*Attorney, Agent, or Firm*—Salter & Michaelson

[57] ABSTRACT

A medical dressing system consists of top and bottom protective sheets sealed around the peripheral edges thereof, and a medical dressing disposed between the top bottom sheets. The medical dressing is arranged between the sheets in a face-up manner such that the dressing is presented for application to a predetermined body part when the top sheet is removed. The top sheet includes line markings which outline the predetermined body part onto which the enclosed dressing is to be applied, and the dressing is aligned with the line markings so that the dressing is properly positioned for application onto the predetermined body part when the dressing system is positioned beneath the predetermined body part. The top sheet further includes a longitudinal centered perforation for sequentially removing first and second halves of the top sheet to expose the enclosed dressing. In this connection, the top sheet includes first and second pull tabs secured to opposing sides edges of top sheet perpendicular to the longitudinal perforation to facilitate removal of the top sheet. A method of applying a medical dressing consists of positioning the described dressing system beneath said predetermined body part, aligning the predetermined body part with line markings on the top sheet, sequentially removing the first and second halves of the top sheet along the perforation line to expose the enclosed dressing, and applying the dressing to the predetermined body part.

11 Claims, 4 Drawing Sheets

5,792,088

1

MEDICAL DRESSING SYSTEM

BACKGROUND AND SUMMARY OF THE INVENTION

The instant invention relates to medical dressings, and more particularly to a medical dressing system, and a method of applying a medical dressing.

Surgical dressings, compression dressings, and support garments are commonly used in all types of medical procedures for the multiple purposes of protecting a wound or incision, applying pressure to the treated area, and absorbing bodily fluids. For purposes of this specification the term "medical dressing" is intended to cover all types of dressings, including surgical dressings, compression dressings, absorbent dressings, support garments, etc.. Medical dressings, in general, are individually packaged in sterile packages for easy availability and application. Use of the existing medical dressings normally requires opening of the sterile package, and application of the dressing to the subject area after the medical procedure is completed. However, it has been found that application of medical dressings in many types of surgical procedures often requires significant movement of the patient, and manipulation of the dressing in order to properly position of dressing onto the patient. Furthermore, movement of such patients, and manipulation of the dressing often requires the attention of more than one care giver. Still further, excessive movement and manipulation often causes the patient undue pain and discomfort. For example, in a surgical procedure involving the chest area, the patient is normally operated on while lying on his/her back. After the procedure is complete, a chest dressing is applied to the patient. However, application of a chest dressing requires movement of the patient to a sitting position to enable care givers to position and secure the chest dressing around the patient's torso area. It is clear that movement of the patient from the lying to the sitting position immediately after surgery causes significant discomfort.

The instant invention provides a medical dressing system which can be placed beneath a patient prior to a surgical procedure, which will protect the medical dressing from fluid contamination prior to application, and which is easily applied to the patient immediately after a surgical procedure without undue movement of the patient and/or manipulation of the dressing by the care giver. The medical dressing system generally comprises top and bottom protective sheets sealed around the peripheral edges thereof, and a medical dressing disposed between the top bottom sheets. The medical dressing is arranged between the sheets in a face-up manner such that the dressing is presented for application to a predetermined body part when the top sheet is removed. The top sheet includes line markings which outline the predetermined body part onto which the medical dressing is to be applied, and the medical dressing is aligned with the line markings so that the medical dressing is properly positioned for application onto the predetermined body part when the medical dressing system is positioned beneath the predetermined body part. The top sheet further includes a longitudinal, centered perforation for sequentially removing first and second halves of the top sheet to expose the enclosed medical dressing. In this connection, the top sheet includes first and second pull tabs secured to opposing sides edges of top sheet perpendicular to the longitudinal perforation to facilitate removal of the top sheet. In use, the subject medical dressing system is positioned beneath a predetermined body part prior to a medical procedure,

2 wherein the predetermined body part is aligned with the line markings on the top sheet of the dressing system. The protective top and bottom sheets protect the enclosed dressing from contamination from bodily and irrigation fluids during the medical procedure. After the procedure is completed, the first and second halves of the top sheet are sequentially removed along the perforation line to expose the enclosed dressing, and the dressing is applied to the predetermined body part.

Accordingly, among the objects of the instant invention are: the provision of a medical dressing system which can be placed beneath a patient prior to a surgical procedure; the provision of a medical dressing system which protects the dressing from fluid contamination prior to application; and the provision of a medical dressing system which is easily applied to the patient without undue movement of the patient and/or manipulation of the dressing by the care giver immediately after the surgical procedure thus reducing the manpower necessary for post-operative care of the patient.

Other objects, features and advantages of the invention shall become apparent as the description thereof proceeds when considered in connection with the accompanying illustrative drawings.

DESCRIPTION OF THE DRAWINGS

In the drawings which illustrate the best mode presently contemplated for carrying out the present invention.

DESCRIPTION OF THE PREFERRED EMBODIMENT

Figure 1:
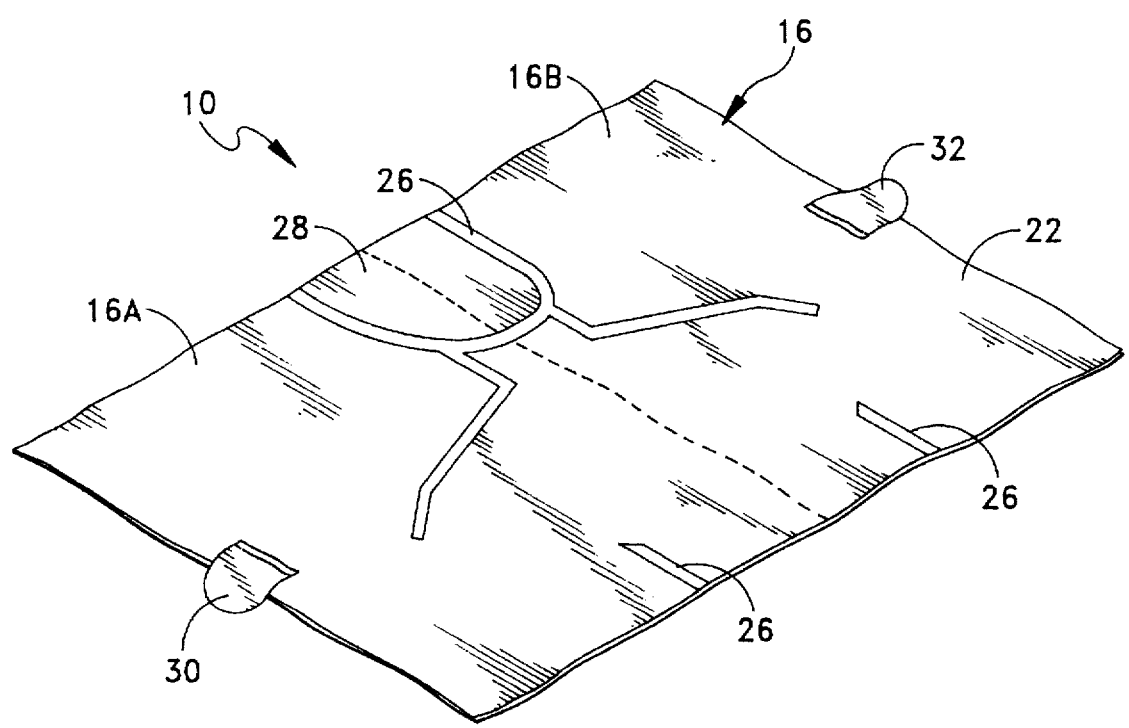
FIG. 1 is a perspective view of the medical dressing system of the instant invention.

Referring now to the drawings, the medical dressing system of the instant invention is illustrated and generally indicated at 10 in FIGS. 1–5. As will hereinafter be more fully described, the instant medical dressing system 10 enables placement of a medical dressing generally indicated at 12 beneath a predetermined body part prior to a surgical procedure, proper alignment of the dressing 12 beneath the body part while still in its packaging, and easy application of the dressing 12 without significant movement of the patient 14 and/or manipulation of the dressing 12.

The instant medical dressing system 10 comprises top and bottom protective sheets, 16 and 18 respectively, which are sealed around their peripheral edges, and a medical dressing 12 disposed therebetween. The particular medical dressing 12 disclosed herein, and illustrated in the drawings, comprises a support bra 20 which is typically utilized after a breast surgery to compress the breasts, and hold absorbent materials in position. While the drawings and disclosure only specifically recite the above-noted support bra 20 as the preferred medical dressing 12, it is to be understood that a plurality of different types of medical dressings, such as surgical dressings, compression dressings, absorbent dressings and other surgical garments, for all parts of the body, are also contemplated within the scope of the invention. The support bra 20 is a front closure type bra which is commonly known in the art, and therefore it will not be described in further detail. The support bra 20 is arranged between the sheets 16, 18 in a face-up manner such that the bra 20 is presented for application around a patient's chest area when the top sheet 16 is removed.

Figure 6:
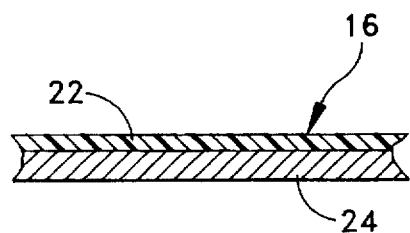

The top and bottom protective sheets 16, 18 preferably comprise a multi-layer sheet material having an outer layer 22 which is impervious to fluids, such as a plastic film material, and an inner absorbent layer 24, such as a layer of gauze material (See FIG. 6). The support bra 20 is received on top of the inner layer 24 of the bottom sheet 18, and is preferably temporarily fixed in position at selected locations (not shown) on the bottom sheet 18 by means of a mild adhesive (not shown), although other methods of temporarily fixing the bra 20 in position are also suitable. In this regard, the adhesive tacking prevents movement of the support bra 20 once properly positioned on the bottom sheet 18, and further allows the bra 20 to be easily detached from the bottom sheet 18 for application to the patient 14.

Figure 2:
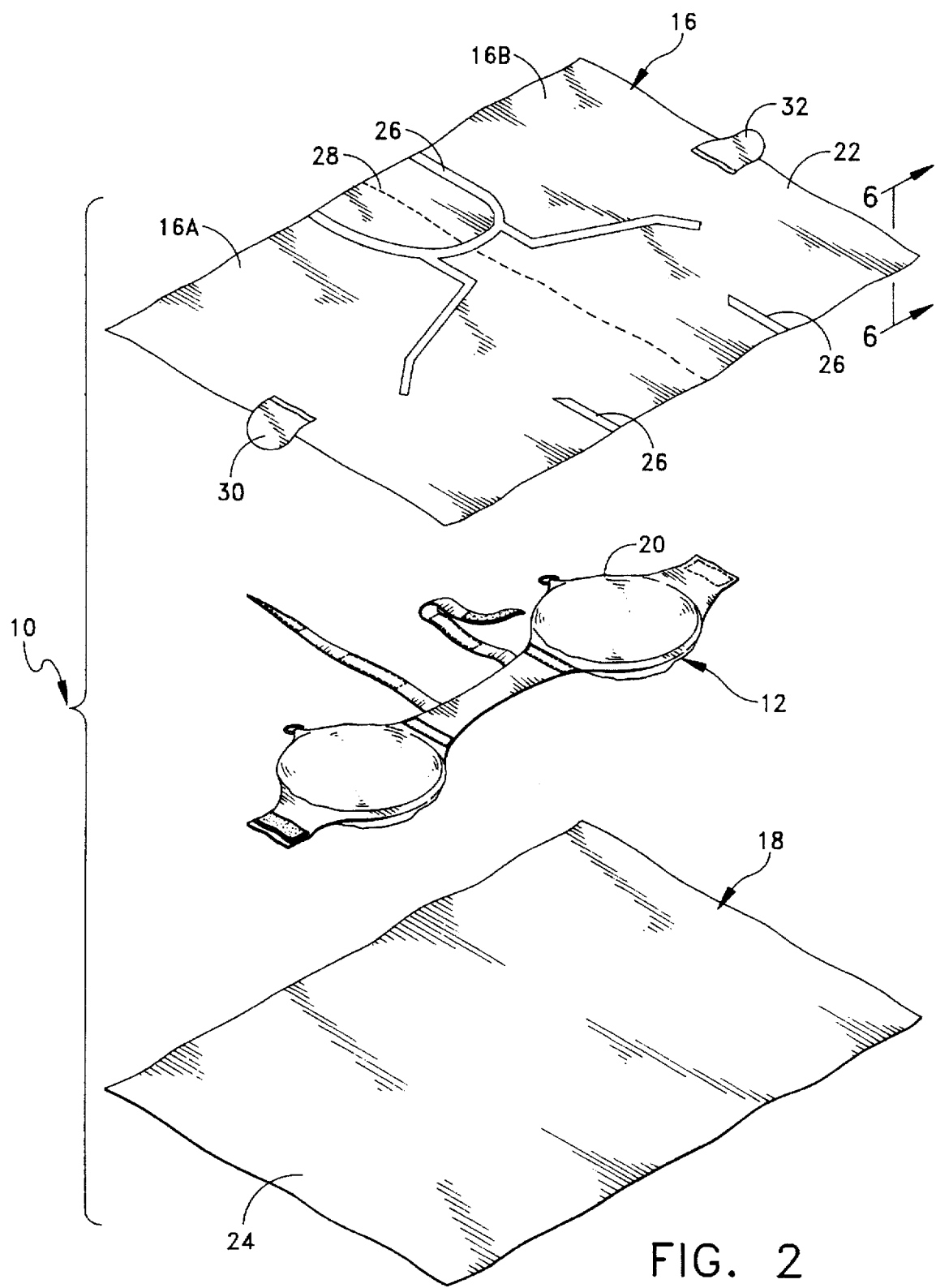
FIG. 2 is an exploded perspective view thereof.
Figure 3:
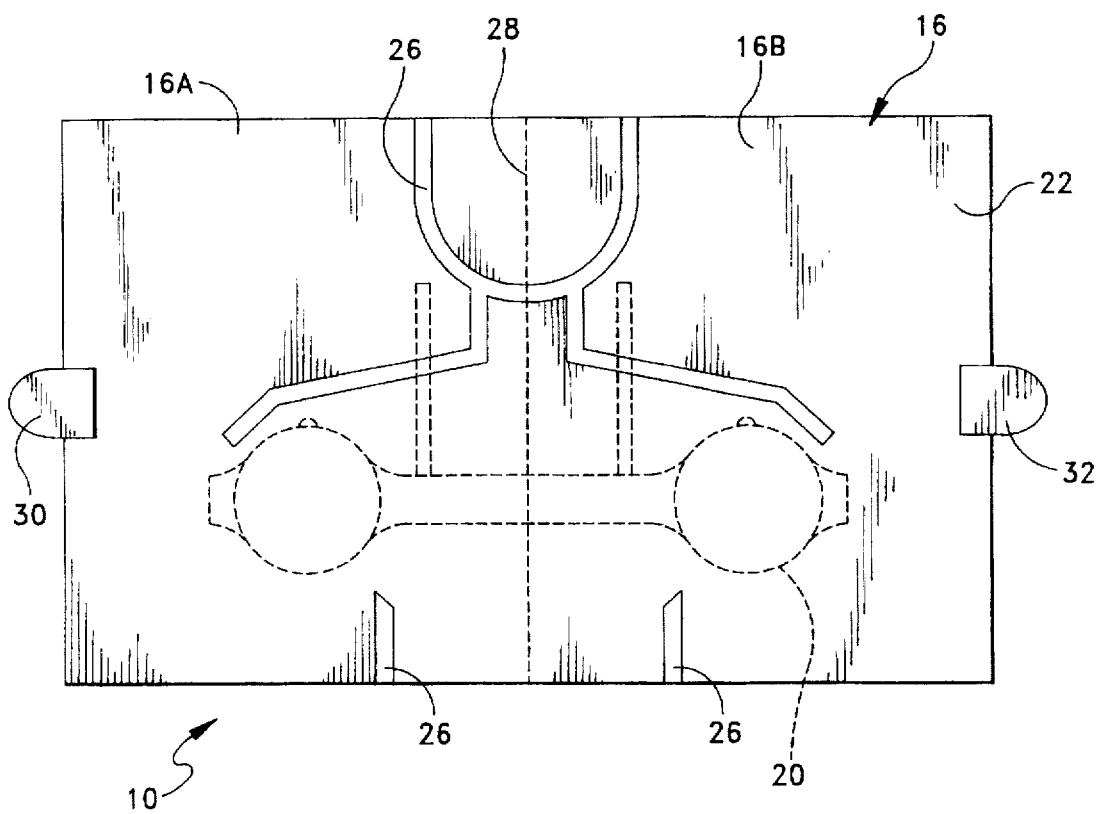
FIG. 3 is a plan view of the medical dressing system with the medical dressing shown in broken lines.

The outer surface 22 of the top sheet 16 is preferably provided with line markings 26 which outline the shape of a predetermined body part onto which the medical dressing 12 is to be applied. The medical dressing 12 is aligned with the line markings 26 so that the dressing 12 is properly position for application onto the predetermined body part when the medical dressing system 10 is positioned beneath the predetermined body part. More specifically, as illustrated in FIGS. 1 and 2, the illustrated line markings 26 are in the outline of a person's chest and head area. The support bra 20 on the bottom sheet 18 is aligned with the line markings 26 (See FIG. 3) so that the bra 20 is properly positioned for application onto the patient's torso area when the medical dressing system 10 is positioned beneath the patient's back.

The top sheet 16 further includes a longitudinal perforation 28 extending down the centerline of the dressing system package. Preferably, the perforation line 28 is aligned parallel to the longitudinal extent of the body part onto which the dressing 12 is to be applied, and extends along the centerline thereof. For example, in FIGS. 1 and 2, it can be seen that the perforation line 28 extends along the longitudinal centerline of the patient's head and chest area. The perforation 28 divides the top sheet into first and second halves, 16A, 16B and enables sequential removal of the first and second halves 16A, 16B to expose the enclosed dressing 12 without significant movement of the patient 14. In this connection, the top sheet 16 preferably includes first and second pull tabs 30, 32 secured to opposing sides edges of top sheet 16 perpendicular to the longitudinal perforation 28 to facilitate removal of the first and second halves 16A, 16B of the top sheet 16.

In use, the dressing system 10 is positioned beneath a predetermined body part prior to a medical procedure, and the predetermined body part is aligned with the line markings 26 on the top sheet 16 of the dressing system 10. The plastic outer layers 22 of the protective top and bottom sheets 16, 18 protect the dressing 12 from contamination from bodily fluids during the medical procedure. After the procedure is completed, the first and second halves 16A, 16B of the top sheet 16 are sequentially removed along the perforation line 28 to expose the surgical dressing 12, and the surgical dressing 12 is applied to the predetermined body part.

Figure 4:
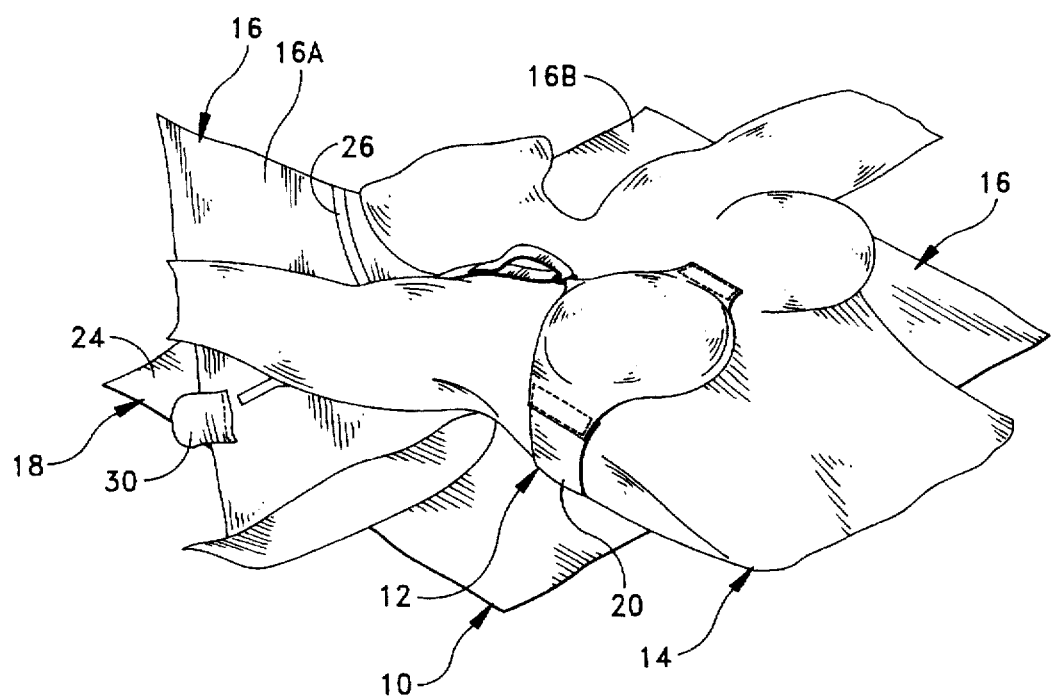
FIG. 4 is a perspective view of the medical dressing system in use, with the first half of the top sheet being removed along its perforation line.
Figure 5:
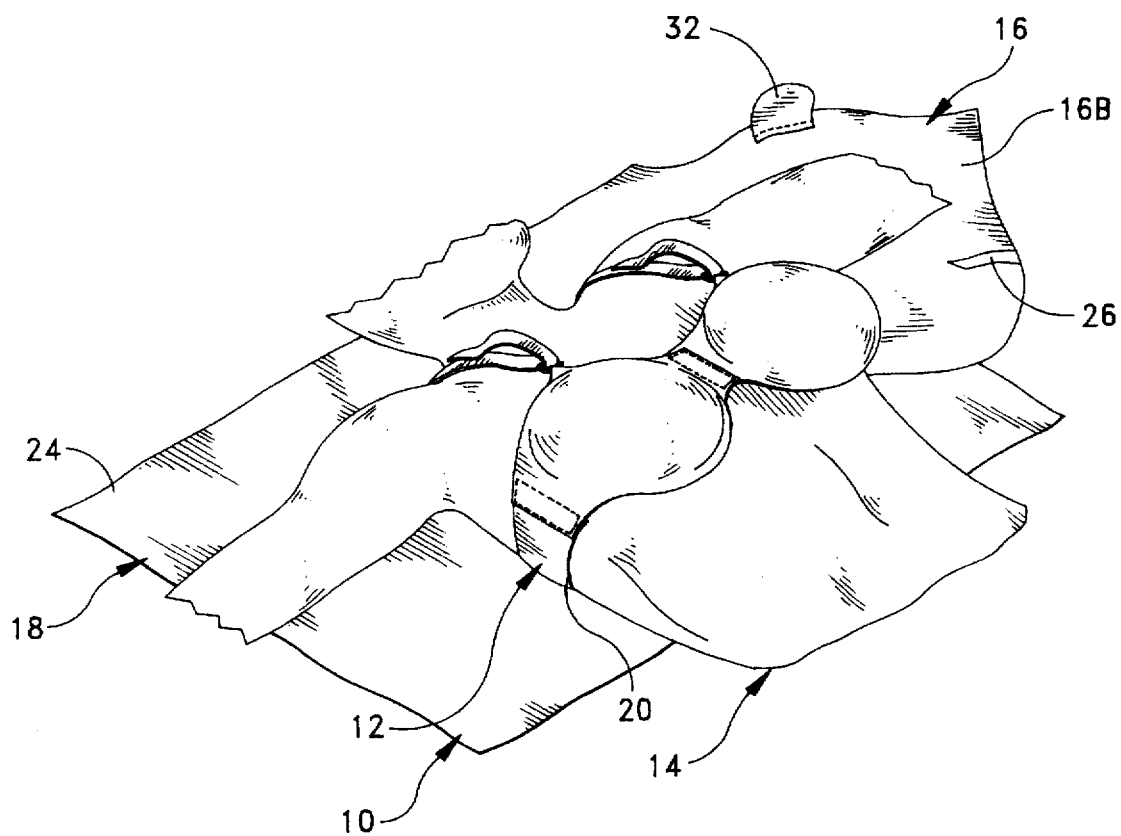
FIG. 5 and 6 are other views thereof with the second half of the top sheet being removed and the medical dressing being applied to the patient.

Referring to FIGS. 4, and 5, the instant dressing system 10 is positioned beneath the back of the patient 14 prior to the breast surgery, and the patient's torso and head are aligned over the line markings 26 on the top sheet 16 so that the support bra 20 will be properly positioned for application after the surgical procedure is completed. Since the support bra 20 is enclosed between the top and bottom protective sheets 16, 18, the sheets 16, 18 protect the support bra 20 from contamination and soiling from bodily fluids, for example blood, and/or irrigation fluids. After the surgical procedure is completed, the right shoulder of the patient 14 is lifted slightly (FIG. 4) wherein the care giver now can grasp the pull tab 30 and remove the first half 16A of the top sheet 16. The left shoulder of the patient 14 is then lifted to facilitate access to the pull tab 32 and removal of the second half 16B of the top sheet 16 to thereby completely expose the support bra 20. Since the patient 14 has already been aligned with the markings 26 on the top sheet 16 of the dressing system 10, the support bra 20 is already in proper position for application to the patient 14 without further movement of the patient 14, or undue manipulation and positioning of the support bra 20.

As stated previously, the invention is intended to cover a wide variety of different medical dressings 12 for different body parts. For example, the dressing 12 may comprise a leg dressing, wherein the markings on the top sheet would outline the portion of the leg onto which the leg dressing is to be applied. In this regard, the patient's leg is properly positioned on top of the dressing system, the top sheet halves are removed by pulling on the pull tabs, and the dressing is exposed for application.

It is further noted that the instant dressing system also has application in field type trauma dressings wherein a care giver is required to bandage a wound outside of a hospital situation. The instant dressing system would be highly efficient in properly placing the dressing onto trauma patients and facilitating rapid medical care.

It can therefore be seen that the instant invention provides a highly effective, and novel surgical dressing system 10 which facilitates application of a dressing 12 onto the patient and reduces excessive movement of the patient for application of a dressing 12. In this regard, the dressing system 12 includes markings 26 on the outside of a protective sheet 16 for properly aligning the enclosed dressing 12 for application onto the patient. The protective sheets 16 enable the dressing 12 to be placed beneath the patient prior to the surgical procedure, thus reducing the need to excessively move the patient immediately after a surgery. For these reasons, the instant invention is believed to represent a significant advancement in the art which has substantial commercial merit.

While there is shown and described herein certain specific structure embodying the invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

We claim:

1. A medical dressing system comprising:
   top and bottom protective sheets each having a peripheral edge, said top and bottom protective sheets being sealed around the peripheral edges thereof; and
   a medical dressing disposed between said top and bottom protective sheets, said medical dressing having inner and outer sides and further having a specific configuration which is suitable for applying the medical dressing to a predetermined body part, said medical dressing being arranged in a face-up manner between said top and bottom protective sheets such that the inner side of the medical dressing is presented for application to a predetermined body part when said top sheet is removed, said top protective sheet including line markings outlining said predetermined body part onto which said medical dressing is to be applied, said medical dressing being aligned with said line markings so that said medical dressing is properly positioned for application onto said predetermined body part when said medical dressing system is positioned beneath said predetermined body part and said body part is aligned with said line markings on said top sheet, said top protective sheet further including a longitudinal perforation for removing said top sheet in sections from the bottom protective sheet.

2. The medical dressing system of claim 1, wherein said top and bottom protective sheets are impervious to fluids.

3. The medical dressing system of claim 1, wherein said longitudinal perforation is aligned generally parallel to a longitudinal extent of said predetermined body part.

4. The medical dressing system of claim 3, wherein said longitudinal perforation is arranged along a longitudinal centerline of said top sheet.

5. The medical dressing system of claim 1 further comprising first and second pull tabs secured to the peripheral edges of the top sheet on opposing sides of said longitudinal perforation.

6. The medical dressing system of claim 5 wherein said pull tabs are arranged along side edges of the top sheet and extend perpendicular to the longitudinal perforation.

7. The medical dressing system of claim 4 further comprising first and second pull tabs secured to the outer peripheral edges of the top sheet on opposing sides of said longitudinal perforation.

8. The medical dressing system of claim 5 wherein said pull tabs are arranged along side edges of the top sheet and extend perpendicular to the longitudinal perforation.

9. The medical dressing system of claim 1 further comprising means for releasably securing said medical dressing between said top and bottom protective sheets to prevent movement of said medical dressing relative to said line markings.

10. The medical dressing system of claim 10 wherein said means for releasably securing said medical dressing comprises an adhesive substance applied to selected portions of said medical dressing.

11. A method of applying a medical dressing to a predetermined body part comprising the steps of:

positioning a medical dressing system beneath said predetermined body part, said medical dressing system comprising top and bottom protective sheets and a medical dressing disposed between said top and bottom protective sheets, said top and bottom protective sheets each having a peripheral edge wherein the top and bottom sheets are sealed to each other around said peripheral edge, said medical dressing having inner and outer sides and further having a specific configuration which is suitable for applying the medical dressing to a predetermined body part, said medical dressing being arranged in a face-up manner such that the inner side of the dressing is presented for application to said predetermined body part when said top sheet is removed;

aligning said predetermined body part with line markings on the top sheet of said medical dressing system which outline said predetermined body part, said medical dressing being aligned with said line markings;

sequentially removing first and second halves of said top sheet along a perforation line in said top sheet to thereby expose an inner side of said medical dressing; and applying said medical dressing to said predetermined body part.

* * * * *